April 5, 1955 R. G. JELLY Plant Pat. 1,374
ROSE PLANT
Filed Aug. 6, 1954
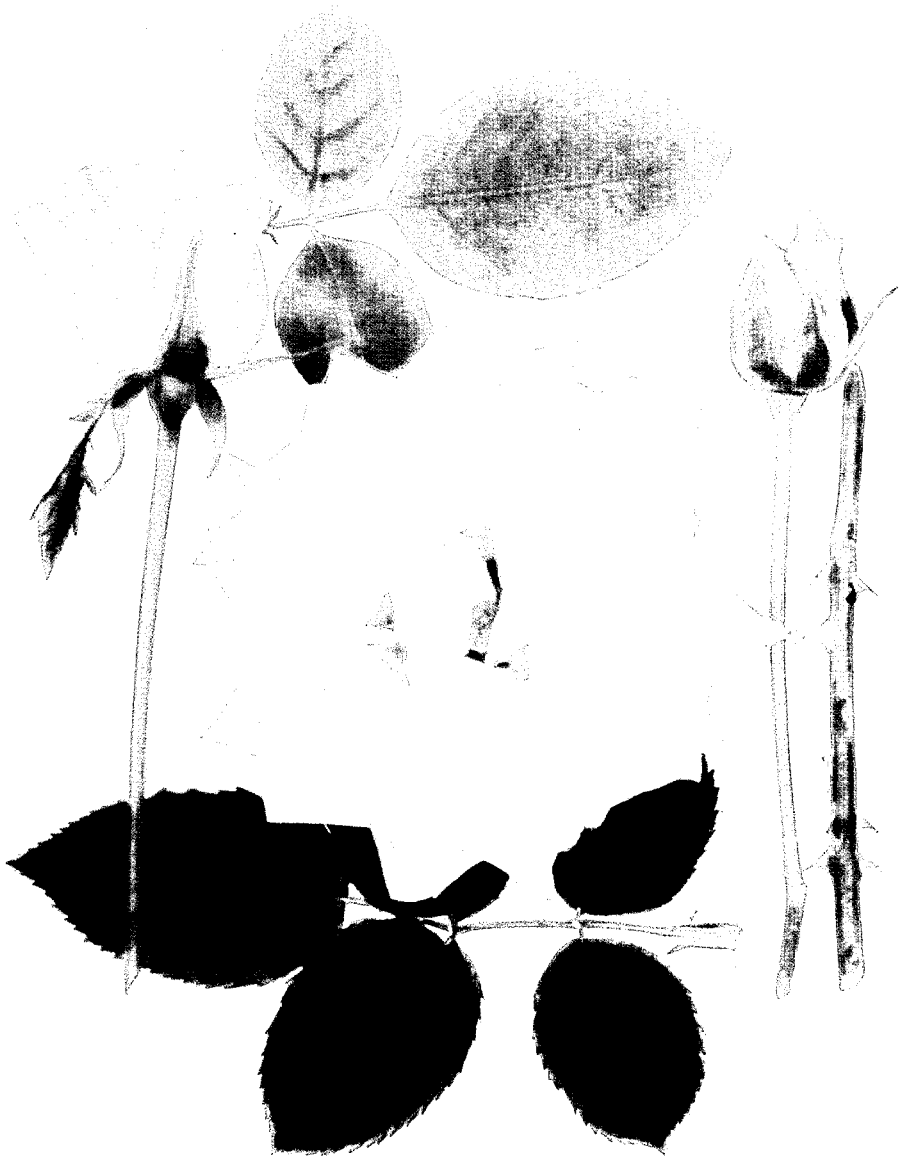
Inventor.
R. G. Jelly
By: Robb & Robb
Attorneys.

United States Patent Office

Plant Pat. 1,374

Patented Apr. 5, 1955

1,374

ROSE PLANT

Robert G. Jelly, Richmond, Ind., assignor to E. G. Hill Co., Inc., Richmond, Ind., a corporation of Indiana Application August 6, 1954, Serial No. 448,402

1 Claim. (Cl. 47—61)

The present invention relates to a new and distinct variety of rose plant of the hybrid tea class, which was originated by me by crossing an unnamed and unpatented seedling with the variety "Golden Rapture" (unpatented).

The primary objective in making this cross was to produce a new variety of rose plant which bears flowers of a clear pink color and type, as desired and long sought by commercial floriculturists, combined with good foliage characteristics and good productivity of its flowers. This objective was fully achieved, as evidenced by the fact that the new variety has inherited from its pollen parent, "Golden Rapture," the excellent and vigorous habits of growth, with glossy and highly attractive foliage which is in a class by itself, combined with abundant production of clear pink, full and heavy-petaled flowers of uniform and invariable color. The lack of variation of the flower color in my new variety is highly desirable and important in the commercial production of cut flowers, and makes my new variety superior to the variety "Golden Rapture" which produces many off-color blooms so typical of most pink roses that are commercially grown at the present time. The flower color is deeper than that of the well-known variety "Pink Bountiful" (Plant Patent No. 601), and the clarity of the pink color, combined with the glossy foliage, excellent growth and high flower productivity of my new variety represents a unique and highly desirable combination that is distinctly different from anything heretofore available to rose growers in the general class of pink roses.

Asexual reproduction of my new variety by grafting at Richmond, Indiana, and also by budding at San Leandro, California, shows that the foregoing characteristics and distinctions come true to form and are established and transmitted through succeeding propagations.

The accompanying drawing shows typical specimens of the stems, foliage and flowers of my new variety, the latter being shown in different stages of development, as depicted in color as nearly true as it is reasonably possible to make the same in a color illustration of this character.

The following is a detailed description of my new variety, with color terminology in accordance with Ridgway's Color Standards and Nomenclature:

Type: Bush; greenhouse; seedling; for cut flowers.
Class: Hybrid tea.
Breeding: Seedling.
*Seed parent.*—An unnamed seedling.
*Pollen parent.*—"Golden Rapture."
Propagation: Holds its distinguishing characteristics through succeeding propagations by both grafting and budding.

FLOWER

Locality where grown and observed: Richmond, Indiana.
Flowers borne: 1 to stem; on strong stems of medium length.
Quantity of bloom: Free, in greenhouse.
Continuity: Continuous, in greenhouse.
Fragrance: Moderate; sweetbriar.
Bud:
*Peduncle.*—Short; medium diameter; strong; erect; slightly rough; no thorns or hairs, but with a few prickles colored Pale Yellow Green, Plate V. Color—Lettuce Green, Plate V.
*Before calyx breaks.*—Size—Medium. Form—Short-pointed; ovoid; without a conspicuous neck; without foliaceous appendages on the surface of the bud; with slender, much-cut foliaceous parts extending beyond the tip of the bud equal to ¼ or more of its length. Color—Lettuce Green, Plate V.
*As calyx breaks.*—Color—Oil Green, Plate V.
*As first petal opens.*—Size—Medium large. Form—Short-pointed. Color: Outside—Rose, Plate XII, shaded to Ochraceous Orange, Plate XV, with a Strontian Yellow, Plate XVI base; inside—Rose, Plate XII, with a Barium Yellow, Plate XVI base.
*Opening.*—Opens well in greenhouse; normal reduction in bud size results from periods of prolonged hot weather.
Bloom:
*Size (when fully open).*—Medium; from 4 inches to 5 inches.
*Petalage.*—Double; from 45 to 65 petals; arranged regularly.
*Form.*—Slightly flat and full at first, but becoming high-centered; petals being at first tightly rolled inward, but becoming tightly rolled outward later at maturity.
Petals: Moderately thick; with inside velvety and outside satiny and shiny.
*Shape.*—Outside: Obovate, with apex crenate; with 1 to 3 notches. Intermediate: Obovate, with apex obtuse. Inside: Obovate, with apex lobed with 2 or 3 notches.

This description of a newly opened flower was made from a rose grown in a greenhouse in the month of October, at Richmond, Indiana:

Color:
*Outside petal.*—Outside surface—Tyrian Pink, Plate XII, with edge shaded to Deep Rose Pink, Plate XII, and with an almost white base. Inside surface—Rose, Plate XII, shaded to Deep Rose Pink, Plate XII, with a Sulphur Yellow, Plate V base.
*Intermediate petal.*—Outside surface—Deep Rose Pink, Plate XII, shaded to Rose Pink, Plate XII, with a Sulphur Yellow, Plate V base. Inside surface—Deep Rose Pink, Plate XII, shaded to Rose Pink, Plate XII, with a Maize Yellow, Plate IV base.
*Inner petal.*—Outside surface—Deep Rose Pink, Plate XII. Inside surface—Deep Rose Pink, Plate XII, with an Orange Buff, Plate III base.

This description was made from a rose that was open for 3 days in a greenhouse in the month of October, at Richmond, Indiana:

Color:
*Outside petal.*—Outside surface—Deep Rose Pink, Plate XII, shaded to Mallow Pink, Plate XII, with a Pale Chalacedony Yellow, Plate XVII base. Inside surface—Rose Pink, Plate XII, with a light Chalcedony Yellow, Plate XVII base.
*Intermediate petal.*—Outside surface—Rose Pink, Plate XII, with a Sea Foam Yellow, Plate XXXI base. Inside surface—Rose Pink, Plate XII, shaded to Cameo Pink, Plate XXVI, with a Naphthalene Yellow, Plate XVI base.
*Inner petal.*—Outside surface—Rose Pink, Plate XII. Inside surface—Rose Pink, Plate XII, with a Massicot Yellow, Plate XVI base.
General color effect:
*Newly opened flower.*—Rose, Plate XII.
*3-days open.*—Rose Pink, Plate XII.
Behaviour: Persist, in greenhouse; slight fading.
Flower longevity: Cut roses grown in greenhouse and kept at livingroom temperatures—5 days in October.

PLANT

Foliage:
*Leaves.*—Compound of 5, but sometimes 7, leaflets; normally abundant; medium size; very glossy.
*Leaflets.*—Shape—Ovoid, with apex cuspidate. Base—Obtuse. Margin—Serrate.
*Color.*—Mature: Upper surface—Yew Green, Plate XXXI; under surface—Pistaschio Green, Plate XLI. Young: Upper surface—Cedar Green, Plate VI, with Garnet Brown, Plate I tint and venation. Under surface—Garnet Brown, Plate I, underlain with greenish cast.

*Rachis (the supporting stem of the compound leaf).*—From medium to heavy. Upper side—Grooved; prickly. Under side—Moderately thorny.

*Stipules.*—Medium length; medium width; with points of medium length; recurved toward stem.

Growth:

*Habit.*—Upright; much-branched.

*Growth.*—Free; vigorous.

*Canes.*—Medium diameter.

*Main stems.*—Color—Cress Green, Plate XXXI. Thorns—Several; medium length; hooked downward; with narrow base. Color—Snuff Brown, Plate XXIX. Prickles—None. Hairs—None.

*Branches.*—Color—Calla Green, Plate V. Thorns—several; medium length; hooked slightly downward; with narrow base. Color—Deep Olive Buff, Plate XL. Prickles—None. Hairs—None.

*New shoots.*—Color—From Verona Brown, Plate XXX, to Yellowish Oil Green, Plate V. Thorns—Several; medium length; hooked slightly downward; with narrow base. Color—Pompeian Red, Plate XIII. Prickles—None. Hairs—None.

REPRODUCTIVE ORGANS

Stamens: Medium number; arranged regularly about pistils; tucked in calyx.

Filaments: Medium length; most with anthers.

*Color.*—Amaranth Pink, Plate XII.

Anthers: Small.

*Color.*—Burnt Lake, Plate XII.

Pollen: Abundant.

*Color.*—Ochraceous Orange, Plate XV.

Pistils: Medium number.

Styles: Even; medium length; medium heavy; bunched; columnar.

*Color.*—Nopal Red, Plate I.

Stigma:

*Color.*—Antimony Yellow, Plate XV.

Ovaries: Some protruding from calyx.

Hips: Medium length; from ovoid to globular; with inconspicuous neck; pear-shaped; very smooth; walls thin and dry.

*Color.*—Bittersweet Orange, Plate II.

Sepals: Permanent; medium length; spear-shaped; recurved.

*Color.*—Inside—Asphodel Green, Plate XII; outside—Parrot Green, Plate VI.

Seeds: Many; medium size.

I claim:

A new and distinct variety of rose plant of the hybrid tea class, substantially as herein shown and described, characterized particularly as to novelty by its superior growth, vigor and flower productivity, its very glossy foliage, its full and heavy-petaled flowers of clear pink general color tonality, and the relative absence of variation of the flower color.

No references cited.